(12) United States Patent
Dirksen et al.

(10) Patent No.: US 8,327,521 B2
(45) Date of Patent: Dec. 11, 2012

(54) METHOD FOR PRODUCTION AND USING A CAPACITIVE MICRO-MACHINED ULTRASONIC TRANSDUCER

(75) Inventors: Peter Dirksen, Valkenswaard (NL); Anthonie Van Der Lugt, Waalre (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 188 days.

(21) Appl. No.: 12/678,453

(22) PCT Filed: Sep. 17, 2008

(86) PCT No.: PCT/IB2008/053778
§ 371 (c)(1),
(2), (4) Date: Mar. 16, 2010

(87) PCT Pub. No.: WO2009/037655
PCT Pub. Date: Mar. 26, 2009

(65) Prior Publication Data
US 2010/0207485 A1      Aug. 19, 2010

Related U.S. Application Data

(60) Provisional application No. 60/972,836, filed on Sep. 17, 2007.

(51) Int. Cl.
*H04R 31/00* (2006.01)
(52) U.S. Cl. ........ 29/594; 29/25.41; 29/609.1; 257/704; 257/723; 257/724; 257/729; 381/113; 381/116; 381/171; 381/173; 381/181
(58) Field of Classification Search ............... 29/25.41, 29/592.1, 594, 609.1; 257/704, 723, 724, 257/729, 730; 381/113, 116, 171, 173–178, 381/181, 182, 190, 191, 427, 431
See application file for complete search history.

(56) References Cited

U.S. PATENT DOCUMENTS

| | | |
|---|---|---|
| 6,004,832 A | 12/1999 | Haller |
| 6,426,582 B1 | 7/2002 | Niederer |
| 7,047,814 B2 * | 5/2006 | Zias et al. ............. 73/718 |

(Continued)

OTHER PUBLICATIONS

Ergun, A.S. et al "Capacitive Micromachines Ultrasonic Transducers: Fabrication Technology" IEEE Transactions on Ultrasonics, Ferroelectrics, and Frequency Control, vol. 52, No. 12, Dec. 2005, pp. 2242-2258.

*Primary Examiner* — Paul D Kim
(74) *Attorney, Agent, or Firm* — W. Brinton Yorks, Jr.

(57) ABSTRACT

Methods are provided for production of pre-collapsed capacitive micro-machined ultrasonic transducers (cMUTs). Methods disclosed generally include the steps of obtaining a nearly completed traditional cMUT structure prior to etching and sealing the membrane, defining holes through the membrane of the cMUT structure for each electrode ring fixed relative to the top face of the membrane, applying a bias voltage across the membrane and substrate of the cMUT structure so as to collapse the areas of the membrane proximate to the holes to or toward the substrate, fixing and sealing the collapsed areas of the membrane to the substrate by applying an encasing layer, and discontinuing or reducing the bias voltage. CMUT assemblies are provided, including packaged assemblies, integrated assemblies with an integrated circuit/chip (e.g., a beam-steering chip) and a cMUT/lens assembly. Advantageous cMUT-based applications utilizing the disclosed pre-collapsed cMUTs are also provided, e.g., ultrasound transducer-based applications, catheter-based applications, needle-based applications and flowmeter applications.

22 Claims, 7 Drawing Sheets

U.S. PATENT DOCUMENTS

| | | | |
|---|---|---|---|
| 7,274,623 B2 * | 9/2007 | Bayram et al. | 367/140 |
| 2005/0219953 A1 * | 10/2005 | Bayram et al. | 367/178 |
| 2005/0234342 A1 | 10/2005 | Bayram | |
| 2006/0004289 A1 | 1/2006 | Tian | |
| 2006/0116585 A1 | 6/2006 | Nguyen-Dinh | |
| 2006/0279174 A1 | 12/2006 | Oliver | |

* cited by examiner

METHOD FOR PRODUCTION AND USING A CAPACITIVE MICRO-MACHINED ULTRASONIC TRANSDUCER

BACKGROUND

1. Technical Field

The present disclosure is generally directed towards the field of acoustic imaging, e.g., photoacoustic imaging, ultrasonic imaging, and the like. More particularly, exemplary embodiments of the present disclosure relate to new and useful methods for the production of high-end transducer arrays, e.g., transducer arrays that may be advantageously employed in acoustic imaging applications. Exemplary embodiments of the present disclosure also relate to capacitive micro-machined ultra sonic transducers (cMUTs) that provide improved uniformity and reliability based on the advantageous production methods disclosed herein.

2. Background Art

In acoustic imaging applications, high-end two-dimensional arrays of ultrasound (US) transducers enable active beam steering/focusing and offer/support real-time three-dimensional imaging applications. Furthermore, the quality of such transducer arrays is a key to overall acoustic imaging product performance and often times is a decisive factor in product differentiation. To this end, methods affecting reliable, efficient, low-cost production of US transducer arrays are in high demand.

Current technology for manufacture of US transducer arrays generally involves one of: (i) techniques for fabrication of piezoelectric micro-machined ultrasonic transducers (pMUTs) that generally involve thin-film processes and application of piezoelectric stack technology, and (ii) techniques for fabrication of capacitive micro-machined ultrasonic transducers (cMUTs) that generally involve a sacrificial release process wherein a cavity is created underneath a membrane by depositing a sacrificial layer on the carrier substrate.

In pMUT manufacture, bonded layers of piezoelectric ceramic, composite and simple polymer matching layers are provided. A diamond saw may be used to dice individual elements. Interconnection may be achieved by a conductive layer on the front surface for common, flex traces to element. Alternatively, pMUTs can be made using lithographic techniques, whereby the need for a diamond saw is obviated. Signals are generally transmitted from the pMUT to an ancillary system through coaxial cable or the like. Single crystal manufacture can provide/support improved performance, but at a cost that may not be competitively viable.

Current methods for the production of cMUTs may involve sacrificial etch processes, whereby a vacuum cavity is created beneath a silicon nitride membrane. For an overview of current cMUT-related processing methods, see "Capacitive Micromachined Ultrasonic Transducers: Fabrication Technology," A. S. Ergun, et al., IEEE Transactions on Ultrasonics, Ferroelectrics, and Frequency Control, Vol. 52, (12), December 2005. Wafer bonding techniques for manufacture of cMUTs have also been disclosed.

Figure 1:
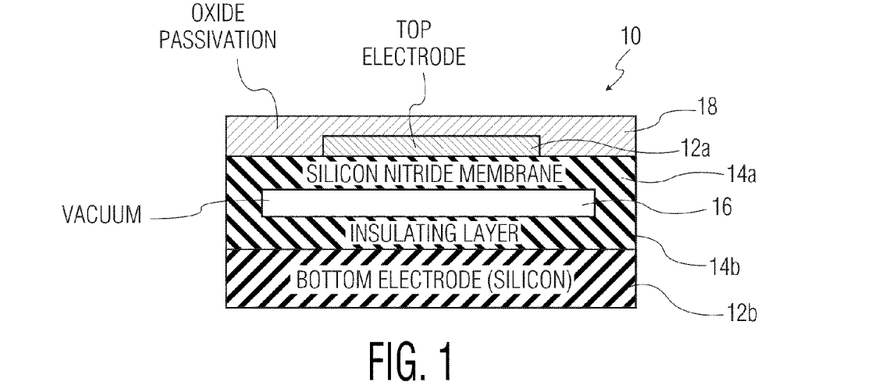
FIG. 1 depicts a schematic cross-section of an exemplary conventional one-dimensional cMUT element.

A schematic cross-section of an exemplary conventional one-dimensional cMUT element 10 is depicted in FIG. 1 (prior art). As depicted therein, a typical cMUT element (uncollapsed) includes (from bottom up) a bottom electrode 12b on a silicon substrate, an insulating layer 14b, a membrane 14a, a top electrode 12a, and an oxide passivation layer 18. Typically, the membrane 14a and insulating layer 14b are configured so as to define a vacuum cavity 16, e.g., a cylindrical cavity, therebetween.

Application of a bias voltage effects a charge which pulls the membrane and substrate closer together. However, if the membrane/substrate are brought too close together, collapse may occur. In traditional production of cMUT arrays, small holes (often times in the sub-100 nm order) and channels are etched through the membrane layer to produce the depicted structure, although larger etched channels (on the order of 2-5 microns) have been disclosed. Relatively expensive and complicated equipment/techniques may be needed to pattern the holes in the membrane for the sacrificial etch, e.g., high-resolution e-beam lithography.

Conventional cMUTs (uncollapsed) carry with them inherent disadvantages, including non-linear behaviour, narrow operating range, low capacitance, and high sensitivity to manufacturing variability. In addition, a relatively high bias voltage is required. It is noted that, for an un-collapsed cMUT, the force on the membrane is proportional to the square of the charge. Thus, increasing the force decreases separation which, in turn, increases capacitance, and (with a voltage bias) increases the charge. Consequently, the membrane will eventually collapse when positive feedback overcomes the rigidity of the membrane; the result of this collapse is formation of a collapsed cMUT.

Collapsed cMUTs have been investigated. For example, collapsed cMUTs have been formed wherein the membrane is collapsed to the bottom of the cavity by applying a DC bias voltage. Collapsed cMUTs can offer improved performance. However, problems specific to collapsed cMUTs have yet to be adequately resolved and/or addressed, e.g., manufacturing-related problems, issues related to array uniformity, and overall reliability. For example, the relatively high voltage needed to produce membrane collapse creates significant complications, e.g., increased cMUT sensitivity to charging. Such relatively high voltages may also negatively impact on associated electronics, e.g., chips.

Thus, a need remains for effective and reliable manufacturing methods for fabrication of collapsed cMUTs that exhibit desirable performance properties on a consistent and cost-effective basis. As will be apparent to persons skilled in the art from the disclosure which follows, the advantageous methods disclosed herein meet this unresolved need and support commercial manufacture of collapsed cMUTs, with the attendant benefits associated therewith.

SUMMARY OF THE DISCLOSURE

Advantageous methods for production of pre-collapsed cMUTs are provided according to the present disclosure. More particularly, exemplary embodiments of the disclosed methods provide for significant cost-effective improvements in standards of manufacture and overall efficacy of collapsed cMUTs. Indeed, exemplary embodiments of the methods disclosed effectively solve previously unresolved problems associated with collapsed cMUTs, including the necessity for a relatively high collapse voltage and a related sensitivity to charging. While exemplary embodiments of the present disclosure generally relate to acoustic imaging applications and, more specifically, photoacoustic (PA) imaging applications, it is specifically contemplated that the methods disclosed herein apply with equal utility and benefit to any field wherein compact transducer arrays may be desirable.

Generally, exemplary embodiments of the present disclosure relate to methods for production of pre-collapsed cMUTs that follow conventional manufacturing steps to form/fabricate nearly completed, conventional cMUTs. These nearly completed cMUTs are generally include groupings, e.g., arrays, of cMUT elements, wherein each individual cMUT element includes (from bottom up) (1) a substrate layer, (2) an electrode plate, (3) a membrane layer, and (4) an electrode.

The substrate layer is typically constructed from an industry standard substrate material such as silicon. In exemplary embodiments of the present disclosure, the electrode plate is circularly configured and embedded in the top face of the substrate layer. The membrane layer is typically configured so as to define a cylindrical cavity between the substrate layer and membrane, whereby the embedded electrode plate is enclosed therewithin. The membrane layer is typically constructed from an industry standard membrane material such as silicon nitride. The electrode ring may be advantageously fixed relative to the top face of the membrane layer such that the center of the electrode ring is positioned directly above the center of the electrode plate. Indeed, the outer diameter of the electrode ring may be substantially equal to the diameter of the circularly configured electrode plate in exemplary implementations. Typically, the electrode ring is configured and dimensioned such that the inner diameter of the electrode ring defines an membrane layer area for patterning and/or etching.

According to the present disclosure, the manufacturing method deviates from conventional cMUT fabrication techniques with respect to final (or near-final) processing steps. More particularly, according to the present disclosure, the conventional steps associated with etching of the sacrificial layer and sealing of the membrane layer are replaced and/or improved upon. Thus, in exemplary embodiments of the present disclosure, methods for production of pre-collapsed cMUTs involve the following steps: (1) obtaining a nearly completed cMUT as described herein, (2) defining a hole through the membrane layer for each cMUT element (wherein the hole is generally defined through the center of the electrode ring), (3) applying a bias voltage (typically a well-defined bias voltage) across the membrane and substrate layers so as to collapse the membrane layer to and/or toward the substrate layer proximate to each hole, and (4) fixing/sealing the collapsed membrane layer relative to the substrate layer.

Dimensional characteristics of the holes defined through the membrane layer according to the disclosed manufacturing method may differ relative to dimensions common to traditional cMUT production. Thus, exemplary hole dimensions defined through the membrane layer may be between about 1 and 25 microns. In exemplary embodiments, the holes have a diameter on the order of 10 to 20 µm, although holes of smaller dimension, e.g., hole diameters on the order of about 3 or 4 microns, may be employed according to the present disclosure. In general, the disclosed holes are patterned such that each hole is defined through the membrane layer at (or substantially near) the center point of the corresponding electrode ring. Of note, the diameter of the hole is smaller than the inner diameter of the electrode ring.

In exemplary implementations of the disclosed manufacturing techniques, the holes are defined/formed through the substrate layer by etching sacrificial layer(s) so as to free the membrane layer. Due to the relatively large size of the holes that may be employed according to the present disclosure, traditional etching techniques that required and/or utilized high resolution e-beam lithography may be advantageously avoided. Instead, exemplary techniques for patterning the holes of the present disclosure include the use of "g-line" or "i-line" lithography, thus cutting costs and providing for a greater degree of array uniformity. As used herein, "g-line" lithography involves UV radiation involving a high intensity line at 436 nm wavelength, and "i-line" lithography involves UV radiation involving a high intensity line at 365 nm wavelength. Alternative techniques for forming/patterning the holes according to the present disclosure employ optical lithography at exemplary wavelengths of 248 nm (deep ultraviolet/DUV), 365 nm, 436 nm and the like.

Still further, e-beam and/or imprint lithography may be employed for hole forming/patterning according to the present disclosure.

Additional advantages are achieved according to the disclosed manufacturing techniques. For example, due to the size of the holes in the disclosed manufacturing technique, higher etching rates may be advantageously achieved relative to traditional etching techniques. In addition, since no channels are necessarily created during the disclosed patterning and etching process for pre-collapsed cMUTs, a near-100% array density is possible.

In exemplary embodiments of the present disclosure, the bias voltage applied across the membrane and substrate layers is a DC coupling voltage is between 10 and 250V, e.g., on the order of approximately 100V. The amount of pre-collapse can be regulated by changing the magnitude of the DC coupling voltage, thus allowing for flexible customization and optimization of array properties. Of note, external electrical contacts may be applied to a wafer during the deposition process for purposes of effecting the desired coupling voltage. Of note, the bias voltage may be reduced following collapse of the membrane layer, provided that the voltage remains sufficient to maintain the collapsed state.

According to the present disclosure, the collapsed membrane is fixed and sealed relative to the substrate, e.g., applying an encasing layer to the collapsed assembly. The encasing layer may be an industry standard material, e.g., $Si_3N_4$. During deposition of the encasing layer, the bias voltage is typically maintained active across the membrane and substrate layers. However, in exemplary embodiments of the present disclosure, the bias voltage may be reduced prior to and/or during the fixing and sealing process. After the encasing layer is applied, the bias voltage becomes unnecessary and may be discontinued or reduced to an operating voltage.

The disclosed manufacturing techniques offer many clear advantages over prior art manufacturing techniques. For example, exemplary methods disclosed herein provide for a higher etching rate of the sacrificial layer relative to conventional means. Furthermore, the disclosed etching/patterning steps may be achieved using relatively inexpensive technology, e.g., g-line lithography or i-line lithography, as opposed to the prior art requirement that high resolution e-beam lithography be employed. Exemplary methods of the present disclosure result in pre-collapsed cMUTs with a near-100% array density, high array uniformity and high collapse uniformity. The collapsed cMUTs fabricated according to the present disclosure also exhibit improved linearity, with substantial elimination of any potential hysteresis loop. Furthermore, the amount of pre-collapse can be effectively regulated by varying the magnitude of the bias voltage. Exemplary methods disclosed also have the advantage of reducing the operating voltage for producing a collapsed cMUT and thus exponentially reducing the charging scale. Still further, continued application of a bias voltage during the fixing/sealing process advantageously prevents potential complications during the post-etching drying process.

The disclosed pre-collapsed cMUTs may be packaged to provide an advantageous assembly. For example, a water proof packaging may be formed to encase and protect a pre-collapsed cMUT of the present disclosure. The disclosed cMUTs may also be combined with a focusing lens to facilitate delivery of emitted waves, e.g., ultrasound, to a desired target.

The present disclosure also extends to advantageous applications of the pre-collapsed cMUTs disclosed herein. Thus, in a first exemplary implementation of the disclosed pre-collapsed cMUTs, an integrated assembly is provided that includes, inter alia, a pre-collapsed cMUT and an integrated circuit/chip that includes, inter alia, beam-steering functionality. The beam-steering chip generally includes various features/functionalities, including a pulse generator, one or more drivers (e.g., to boost output voltage), a pre-amplifier, a processor, and/or input/output control functionality. Integration of a pre-collapsed cMUT and a beam-steering chip advantageously facilitates control/optimization of ultrasound delivery from the pre-collapsed cMUT of the present disclosure. An integrate assembly also supports and/or facilitates operative control and data receipt/processing.

The pre-collapsed cMUTs of the present disclosure have wide ranging, advantageous applications. For example, the pre-collapsed cMUTs may be used in various transducer applications that extend beyond ultrasound transducer implementations. For example, the pre-collapsed cMUTs (whether alone or in combination with an integrated chip/IC) may be employed in various catheter-based applications, needle insertion units, ultrasound flow meter implementations and the like. Indeed, in exemplary catheter-based and/or needle-based implementation, a pre-collapsed cMUT according to the present disclosure may be used to locate an anatomical structure, e.g., vessel, or to otherwise facilitate anatomical navigation. Alternative applications that may operate within or outside the ultrasound regimen may benefit from implementation of the pre-collapsed cMUTs disclosed herein, as will be apparent to persons skilled in the art from the description which follows.

Although the present disclosure is described with reference to exemplary embodiments and implementations thereof, the present disclosure is not to be limited by or to such exemplary embodiments and/or implementations. Rather, the apparatus, systems and methods of the present disclosure are susceptible to various modifications, variations and/or enhancements without departing from the spirit or scope of the present disclosure. Accordingly, the present disclosure expressly encompasses all such modifications, variations and enhancements within its scope.

BRIEF DESCRIPTION OF THE DRAWINGS

To assist those of ordinary skill in the relevant art in making and using the subject matter hereof, reference is made to the appended drawings, wherein.

DESCRIPTION OF EXEMPLARY EMBODIMENTS

Exemplary methods for production of pre-collapsed cMUTs are provided according to the present disclosure. To assist those of ordinary skill in the relevant art in making and using such exemplary methods, appended figures are provided, wherein sequential steps of exemplary manufacturing methods are depicted.

Figure 3:
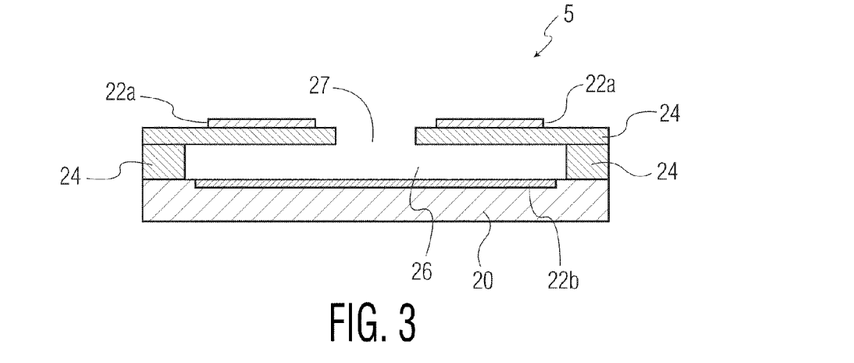
FIG. 3 depicts a schematic cross-section of the element depicted in FIG. 2, wherein a hole has been defined through the membrane layer relative to the center of the electrode ring.
Figure 4:
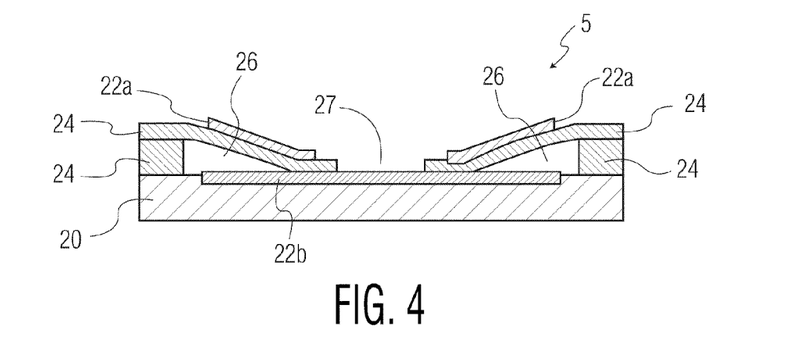
FIG. 4 depicts a schematic cross-section of the element depicted in FIG. 3, wherein a bias voltage has been applied across the membrane and substrate layers so as to collapse the membrane layer relative to the substrate layer.
Figure 5:
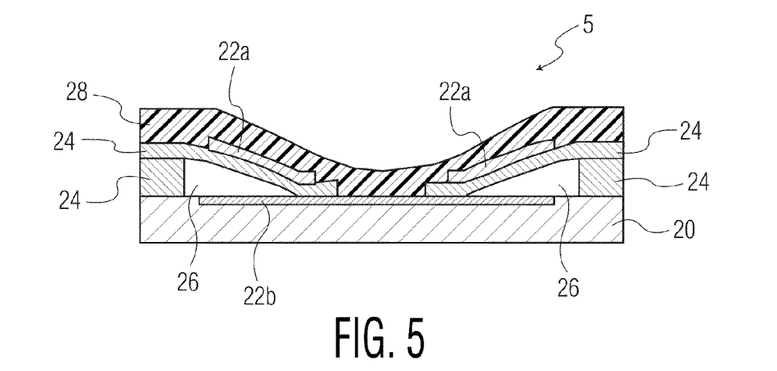
FIG. 5 depicts a schematic cross-section of the element depicted in FIG. 4, wherein the collapsed membrane layer has been fixed and sealed relative to the substrate layer by applying an encasing layer.

Exemplary methods for fabrication of collapsed cMUTs according to the present disclosure typically include the following steps: (1) obtaining a nearly completed cMUT as depicted in FIG. 2, (2) defining at least one hole (and optionally a plurality of holes) through the membrane layer for each cMUT element as depicted in FIG. 3, (3) applying a bias voltage across the membrane and substrate layers so as to collapse the membrane layer relative to the substrate layer as depicted in FIG. 4, and (4) fixing and sealing the collapsed membrane layer relative to the substrate layer as depicted in FIG. 5.

Figure 2:
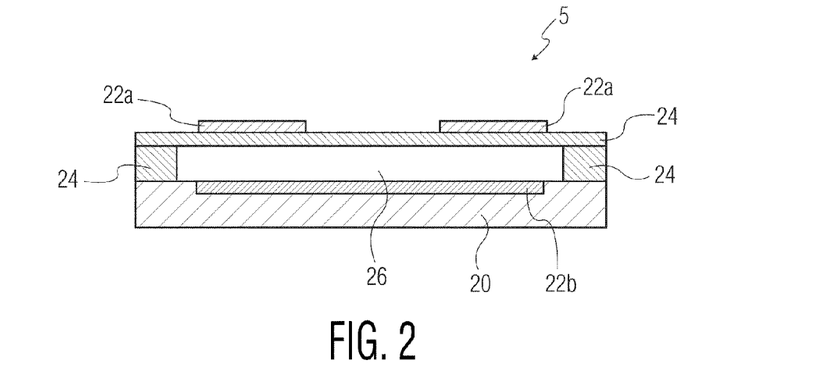
FIG. 2 depicts a schematic cross-section of a single element of a nearly completed cMUT.

With initial reference to FIG. 2, a schematic cross-section of a cMUT element 5 is depicted, wherein the obtained nearly completed cMUT includes a grouping (e.g., an array) of cMUT elements. Exemplary cMUT element 5 includes a substrate layer 20, an electrode plate 22b, a membrane layer 24, and an electrode ring 22a. In the exemplary embodiment, the electrode plate 22b is circularly configured and embedded in the substrate layer 20. In addition, the membrane layer 24 is fixed relative to the top face of the substrate layer 20 and configured/dimensioned so as to define a cylindrical cavity 26 in between the membrane layer 24 and the substrate layer 20. Of note, cylindrical cavity 26 may define alternative geometries, whether in whole or in part. For example, cavity 26 could define a rectangular and/or square cross-section, a hexagonal cross-section, an elliptical cross-section, or an irregular cross-section, as will be apparent to persons skilled in the art.

The bottom electrode 22b is typically insulated with an additional layer (not pictured). The disclosed components may be fabricated from CMOS compatible materials, e.g., Al, Ti, nitrides (e.g., silicon nitride), oxides (various grades), tetra ethyl oxysilane (TEOS), poly-silicon and the like.

Exemplary techniques for producing the disclosed cavity 26 involves defining such cavity in an initial portion of the membrane layer 24 before adding a top face of the membrane layer 24. In the exemplary embodiment depicted in FIG. 2, the diameter of the cylindrical cavity 26 is larger than the diameter of the circularly configured electrode plate 22b. Electrode ring 22a may have the same outer diameter as the circularly configured electrode plate 22b, although such conformance is not required according to the present disclosure. Thus, in an exemplary embodiment of the present disclosure, the electrode ring 22a is fixed relative to the top face of the membrane layer 24 so as to align with the electrode plate 22b below.

With reference now to FIG. 3, a schematic cross-section of exemplary cMUT element 5 is depicted, wherein a hole 27 has been defined through the top face of the membrane layer 24 relative to the center of the electrode ring 22a. As noted previously, hole 27 may be augmented with additional holes to define a plurality of holes. As shown in FIG. 3, exemplary hole 27 is circularly configured with a diameter that is less than the inner diameter of the electrode ring 22a. Hole 27 may be advantageously formed using optical lithography, e.g., g-line lithography, i-line lithography, nano-imprint lithography, and/or e-beam lithography. Hole 27 is typically characterized by a diameter of between about 1 and 25 microns.

With reference now to FIG. 4, a schematic cross-section of exemplary cMUT element 5 is depicted, wherein a bias voltage has been applied across the membrane layer 24 and substrate layer 20 so as to collapse the membrane layer 24 relative to the substrate layer 20. An exemplary resulting angular configuration of the electrode ring 22a can be seen. In the exemplary embodiment depicted in FIG. 4, the top face of the membrane layer 24 proximate to the hole 27 is thus brought into contact with the electrode plate 22b.

With reference now to FIG. 5, a schematic cross-section of exemplary cMUT element 5 is depicted, wherein the collapsed membrane layer 24 has been fixed and sealed relative to the substrate layer 20 and the electrode plate 22b by applying an encasing layer 28 over the top face of the membrane layer 24 and the electrode ring 22a. The final resulting cMUT element 5 is thus an exemplary embodiment of one of many pre-collapsed cMUT elements that may be fabricated according to the disclosed manufacturing methodology. Fabrication of the disclosed cMUT may employ plasma-enhanced chemical vapor deposition (PECVD) and/or low pressure chemical vapor deposition (LPCVD). The disclosed electrode plates/members may be fabricated from a suitable conductive material, e.g., a metallic or non-metallic conductive material.

Figure 6:
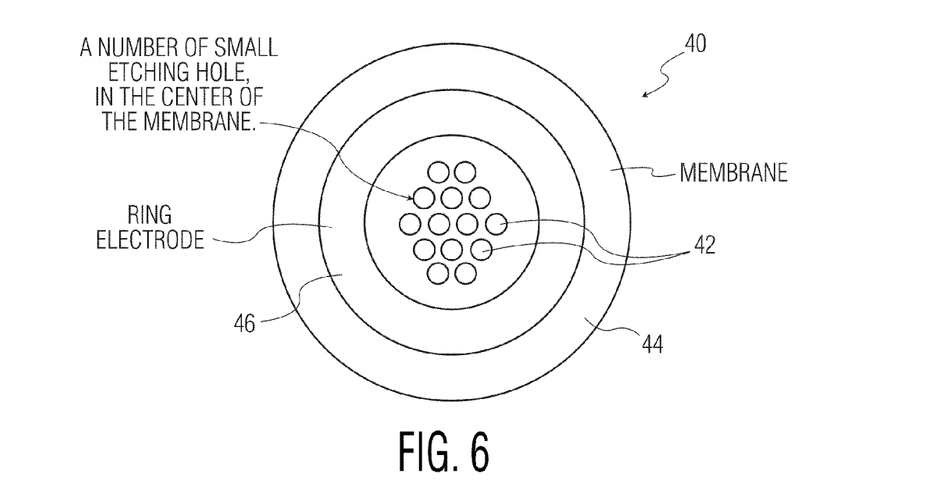
FIG. 6 is a schematic view of an alternative exemplary cMUT of the present disclosure.

An alternative embodiment of the present disclosure is schematically depicted in FIG. 6. Exemplary cMUT 40 includes a plurality of holes 42, e.g., relatively small etched holes, formed in membrane 44. Holes 42 are surrounded by ring electrode 46. Thus, in the alternative embodiment of FIG. 6, a single central hole is replaced by a number of relatively small holes 42 that are positioned approximately in the center of the membrane 44, such holes 42 being located within the inner diameter of the ring electrode 46. Fabrication and functionality of the alternative cMUT 40 of FIG. 6 corresponds to the fabrication/functionality of the previously disclosed exemplary pre-collapsed cMUT (see FIGS. 1-5).

In exemplary embodiments of the present disclosure, an additional insulation layer may be provided on top of bottom electrode 22b. In addition, the metallic bottom electrode 22b may be replaced by a conductive non-metallic layer that provides the same functionality.

Figure 7:
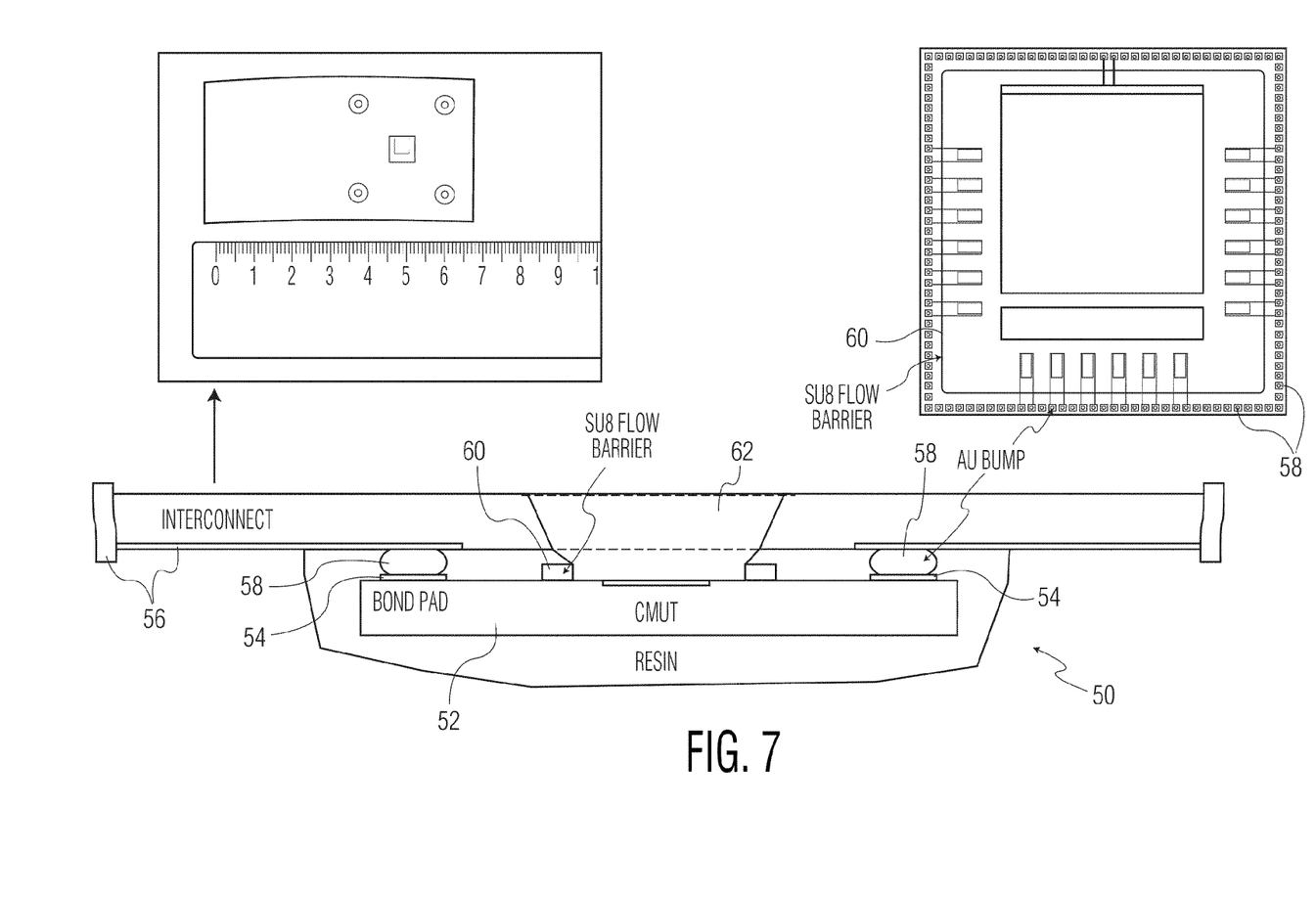
FIG. 7 are schematic views of an exemplary packaged cMUT-containing unit according to the present disclosure.

In further exemplary embodiments of the present disclosure and with reference to FIG. 7, a packaged unit 50 that includes a pre-collapsed cMUT 52 is schematically disclosed. Bond pads 54 are formed along or adjacent the periphery of cMUT 52 and communicate with an interconnect feature 56 through conductive members, e.g., gold bumps 58 that are defined on cMUT 52. A flow barrier 60 is also defined on cMUT 52, internal to gold bumps 58 and surrounding an energy path 62. Energy path 62 facilitates transmission of ultrasound waves and the like. Flow barrier 60 may take the form of an SU-8 flow barrier or other photoresist material. SU-8 is a viscous polymer that defines a commonly used negative photoresist. As assembled, packaged unit 52 advantageously defines a water proof unit having widespread application. Background information related to packaged biosensors is provided in a publication entitled "A new package for silicon biosensors," EMPC 2005, June 12-15, Brugge, Belgium, the contents of which are incorporated herein by reference.

Figure 8:
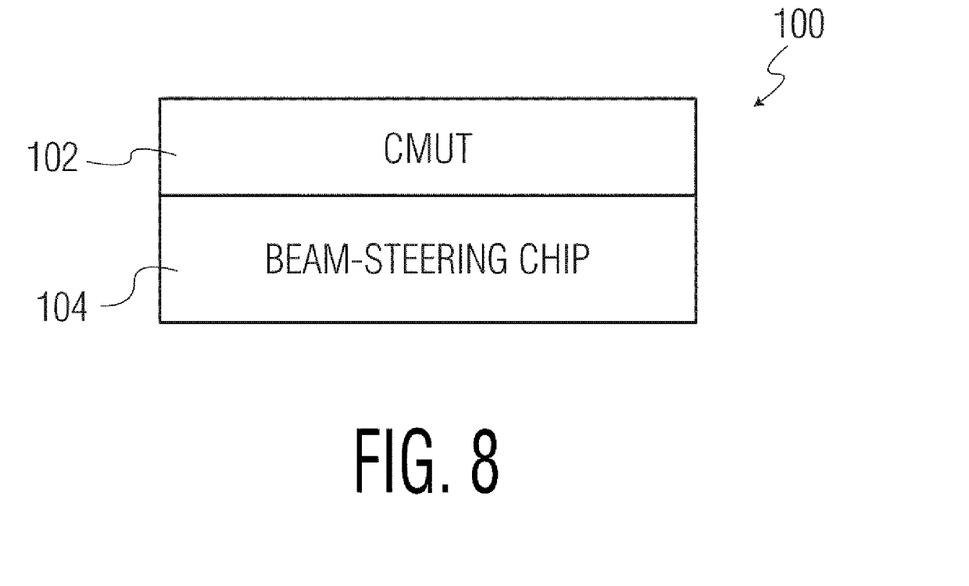
FIG. 8 depicts a schematic view of an exemplary integrated assembly according to the present disclosure that includes a cMUT and a beam-steering chip.

With reference to FIG. 8, a schematic depiction of an exemplary integrated assembly according to the present disclosure is provided. Assembly 100 includes cMUT 102 and beam-steering chip 104 mounted with respect to each other to define an integrated unit. cMUT 102 and beam-steering chip 104 are in communication such that chip 104 provides input to cMUT 102 for ultrasound delivery therefrom. Chip 104 typically includes various features and functionalities, e.g., a pulse generator, one or more drivers (e.g., to boost output voltage), a pre-amplifier, a processor, and input/output control functionality. Design and fabrication of an appropriate beam-steering chip/integrated circuit 104, e.g., an ASIC, is well known to skilled practitioners.

Figure 9:
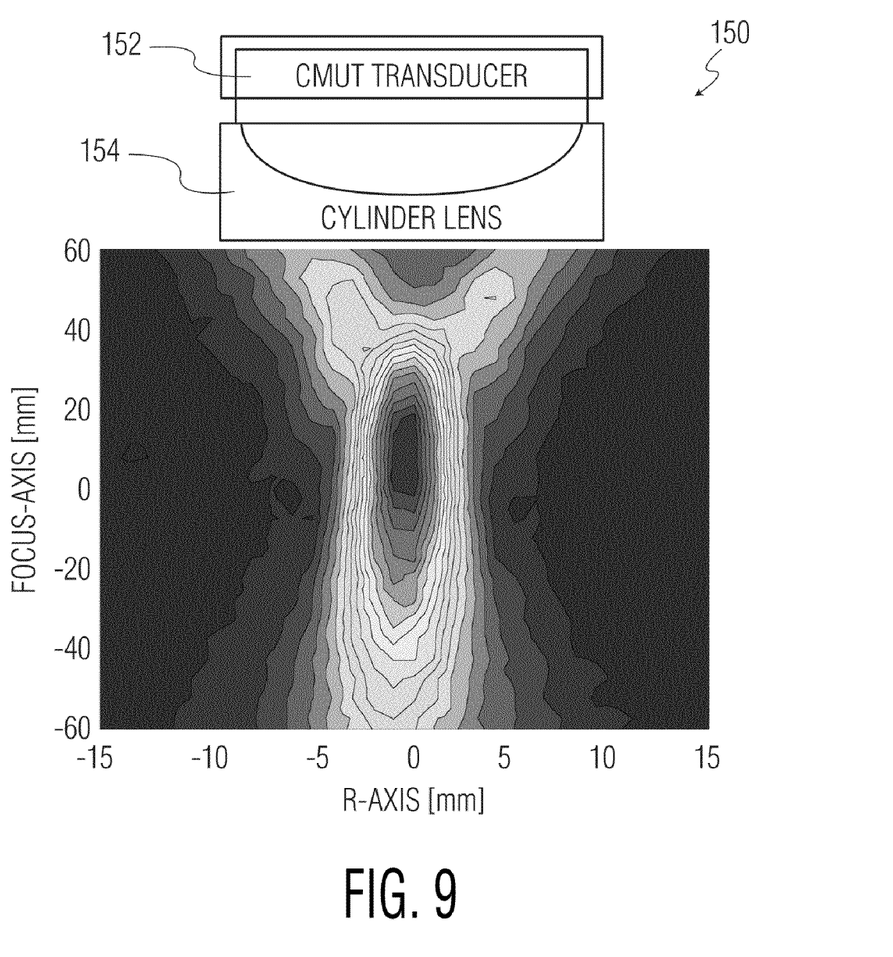
FIG. 9 depicts a schematic view of an exemplary assembly that includes a pre-collapsed cMUT and lens according to the present disclosure.

With reference to FIG. 9, a further assembly 150 including a pre-collapsed cMUT transducer 152 and a lens 154 is schematically depicted. The disclosed lens 154 is generally adapted to focus the emissions from cMUT transducer 152, e.g., ultrasound waves emitted therefrom. Lens 154 may take the form of a plastic unit with appropriate transmission properties.

Figure 10:
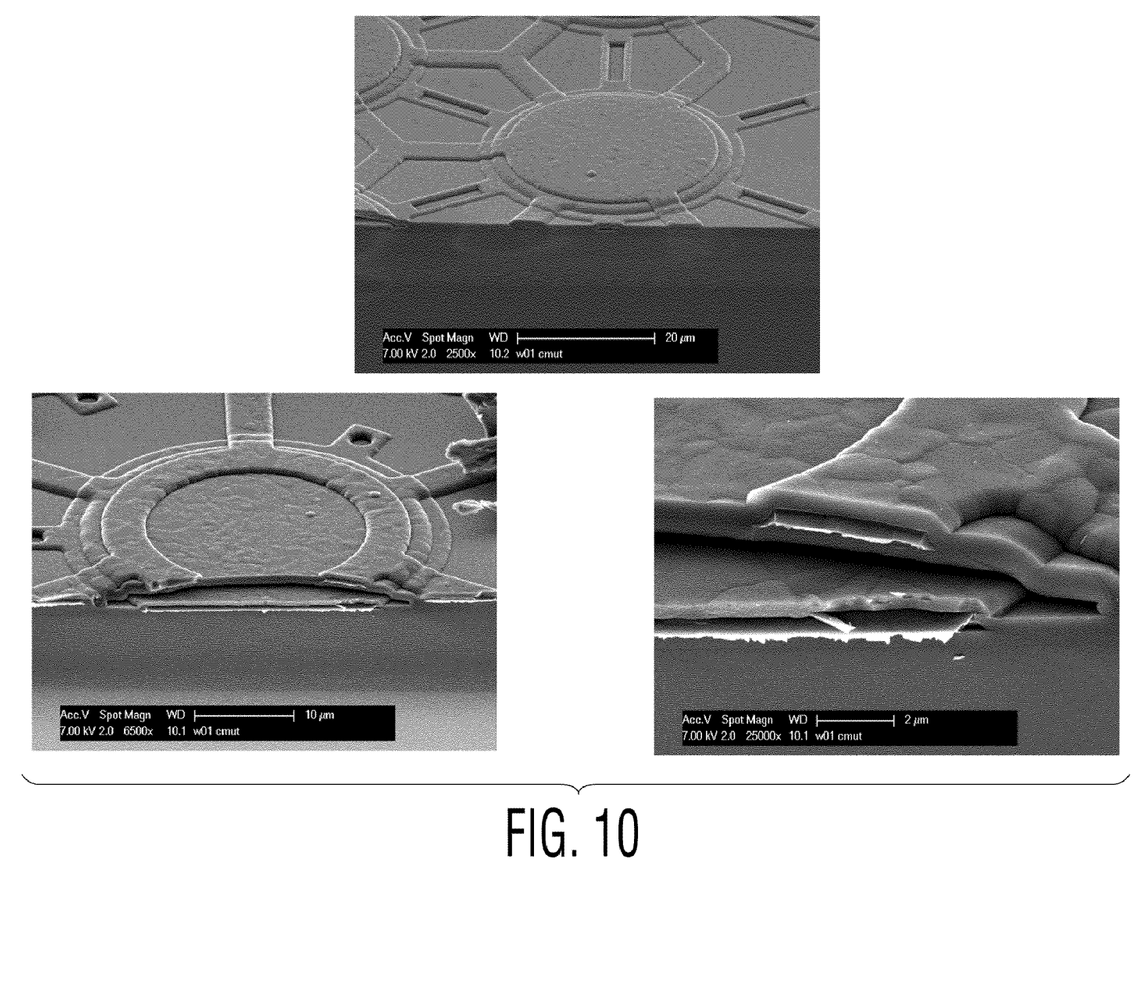
FIG. 10 provides three (3) SEM images of exemplary cMUTs of the present disclosure.
Figure 11:
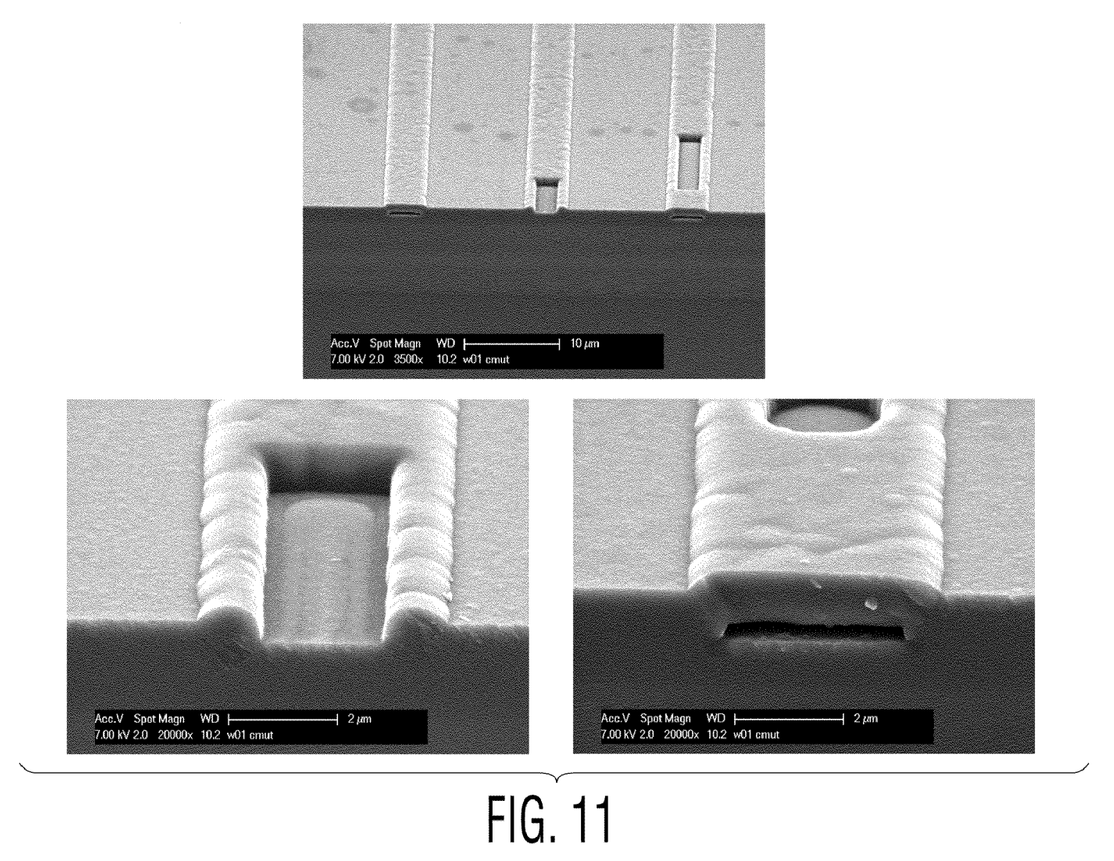
FIG. 11 provides three (3) SEM images related to sealing of etching holes of a cMUT according to the present disclosure.

SEM images associated with the present disclosure are provided in FIG. 10 and FIG. 11 hereto. FIG. 10 provides three (3) SEM images related to fabrication of the disclosed cMUTs and FIG. 11 provides three (3) SEM images related to sealing of etching holes associated with the disclosed cMUTs.

The disclosed cMUT fabrication techniques/methods are adapted to produce pre-collapsed cMUTs with broad application and advantageous functionality. For example, the pre-collapsed cMUTs disclosed herein are advantageously adapted to generate ultrasound waves in predetermined frequency ranges, e.g., 1-5 MHz and 5-50 MHz. Alternative frequency ranges may be supported and/or generated with the pre-collapsed cMUTs of the present disclosure. The pre-collapsed cMUTs of the present disclosure have wide ranging, advantageous applications, e.g., in transducer applications that extend beyond ultrasound transducer implementations. Among the exemplary implementations of the pre-collapsed cMUTs are catheter-based applications, needle insertion applications, ultrasound flow meter applications, and the like. The pre-collapsed cMUTs may be employed alone or in combination with an integrated chip/IC to provide additional features/functionalities. In exemplary catheter-based and/or needle-based implementation, a pre-collapsed cMUT may be used to locate an anatomical structure, e.g., a vessel, organ, etc., or to otherwise facilitate anatomical navigation. Alternative applications that may operate within or outside the ultrasound regimen may benefit from implementation of the pre-collapsed cMUTs disclosed herein.

As noted above, although the present disclosure is described with reference to exemplary embodiments and implementations thereof, the present disclosure is not to be limited by or to such exemplary embodiments and/or implementations. Rather, the apparatus, systems and methods of the present disclosure are susceptible to various modifications, variations and/or enhancements without departing from the spirit or scope of the present disclosure. Accordingly, the present disclosure expressly encompasses all such modifications, variations and enhancements within its scope.

What is claimed is:

1. A method for producing a capacitive micro-machined ultrasonic transducer (cMUT), comprising:
   a. providing a cMUT structure, wherein the cMUT structure defines one or more cMUT elements that include: (i) a substrate layer, (ii) an electrode plate, (iii) a membrane layer, and (iv) an electrode ring;
   b. defining at least one hole through the membrane layer for each cMUT element;
   c. applying a bias voltage across the membrane and substrate layers of the one or more cMUT elements so as to collapse the membrane layer relative to the substrate layer; and
   d. fixing and sealing the collapsed membrane layer relative to the substrate layer by applying an encasing layer.

2. The method according to claim 1, further comprising: (i) discontinuing the bias voltage, or (ii) reducing the bias voltage to an operating voltage.

3. The method according to claim 1, wherein the bias voltage is a well-defined DC voltage supplied by a battery.

4. The method according to claim 3, wherein the well-defined DC voltage falls between 10 and 250V.

5. The method according to claim 1, wherein the bias voltage is effective to regulate the amount of collapse.

6. The method according to claim 5, wherein the regulation of the amount of collapse is effective to optimize performance.

7. The method according to claim 1, wherein the at least one hole is between about 1 and 25 microns in diameter.

8. The method according to claim 1, wherein the at least one hole is defined using an optical lithography technique selected from the group consisting of g-line lithography, i-line lithography, nano-imprint lithography and e-beam lithography.

9. The method according to claim 1, wherein the electrode plate is a circular electrode plate fabricated from a metallic or non-metallic conductive material.

10. The method according to claim 9, wherein an outer diameter of the electrode ring is configured and dimensioned to substantially match a diameter of the circular electrode plate and wherein a center of electrode the ring and a center of the circular electrode plate are substantially aligned.

11. The method according to claim 1, wherein the substrate layer comprises silicon.

12. The method according to claim 1, wherein the membrane layer comprises a CMOS compatible material comprising one of silicon nitride, an oxide, tetra ethyl oxysilane (TEOS), or poly-silicon.

13. The method according to claim 1, wherein the encasing layer comprises a CMOS compatible material comprising one of silicon nitride, an oxide, tetra ethyl oxysilane (TEOS), or poly-silicon.

14. The method according to claim 1, wherein the electrode plate is a metallic or non-metallic conductive material.

15. The method according to claim 1, wherein the cMUT is fabricated, at least in part, using plasma-enhanced chemical vapor deposition (PECVD) and/or low pressure chemical vapor deposition (LPCVD).

16. The method according to claim 1, wherein the electrode plate of the cMUT element is fixed relative to a top surface of the substrate layer.

17. The method according to claim 1, wherein the membrane of the cMUT element is fixed relative to a top face of the substrate layer so as to define a cavity between the membrane and the substrate layer.

18. The method according to claim 1, wherein the electrode ring is fixed relative to a top surface of the membrane layer.

19. The method according to claim 1, wherein the at least one hole is defined through the membrane layer relative to a center of the electrode ring.

20. The method according to claim 1, wherein a diameter of the at least one hole is less than an inner diameter of the electrode ring.

21. The method according to claim 1, wherein an area of collapse of the membrane layer is proximate to the hole.

22. The method according to claim 1, wherein the bias voltage is: (i) maintained throughout the fixing and sealing process, (ii) reduced prior to the fixing and sealing process, (iii) reduced during the fixing and sealing process; or (iv) a combination thereof.

* * * * *